(12) United States Patent
Liotta et al.

(10) Patent No.: US 9,335,328 B2
(45) Date of Patent: May 10, 2016

(54) METHOD AND APPARATUS FOR SIGNAL TRANSDUCTION PATHWAY PROFILING

(75) Inventors: Lance A. Liotta, Bethesda, MD (US); Emanuel F. Petricoin, III, Dunkirk, MD (US); Katherine L. Paweletz, Thousand Oaks, CA (US); Alan R. Day, North Potomac, MD (US)

(73) Assignee: Instant Medical Diagnostics, LLC, Potomac, MD (US)

( * ) Notice: Subject to any disclaimer, the term of this patent is extended or adjusted under 35 U.S.C. 154(b) by 1987 days.

(21) Appl. No.: 10/182,354

(22) PCT Filed: Feb. 2, 2001

(86) PCT No.: PCT/US01/03535
§ 371 (c)(1),
(2), (4) Date: Dec. 15, 2006

(87) PCT Pub. No.: WO01/57530
PCT Pub. Date: Aug. 9, 2001

(65) Prior Publication Data
US 2007/0105157 A1  May 10, 2007

Related U.S. Application Data

(60) Provisional application No. 60/179,997, filed on Feb. 3, 2000.

(51) Int. Cl.
*G01N 33/558* (2006.01)
*G01N 33/68* (2006.01)

(52) U.S. Cl.
CPC ........ *G01N 33/6842* (2013.01); *G01N 33/6803* (2013.01); *G01N 33/6845* (2013.01)

(58) Field of Classification Search
None
See application file for complete search history.

(56) References Cited

U.S. PATENT DOCUMENTS

| | | | | |
|---|---|---|---|---|
| 4,327,073 A | * | 4/1982 | Huang | ............................ 436/44 |
| 4,740,468 A | * | 4/1988 | Weng | .................. G01N 33/538 435/7.91 |
| 5,415,994 A | * | 5/1995 | Imrich | .................. B01L 3/5023 435/5 |
| 6,177,401 B1 | * | 1/2001 | Ullrich et al. | ..................... 514/1 |
| 6,197,599 B1 | * | 3/2001 | Chin et al. | ..................... 436/518 |
| 6,203,757 B1 | * | 3/2001 | Lu | .................... G01N 33/54366 422/412 |

OTHER PUBLICATIONS

Signal Pathway diagrams from www.cellsignal.com 2002-2010.*
(Continued)

*Primary Examiner* — Chris L Chin
(74) *Attorney, Agent, or Firm* — Fay Sharpe LLP

(57) ABSTRACT

An assay device for determining the presence of analytes in a cell lysate comprises a porous support member and a plurality of binding reagents arranged and immobilized at multiple reaction sites on the support member. The binding reagents are selected and arranged to assess the status of a selected cellular signal transduction pathway/protein-protein interactive network. In a further aspect, a method for assessing the status of a signal transduction pathway comprises generating a lysate of cells, the lysate retaining one or more pathway molecules present in one or more states and the pathway molecules reflecting signal transduction events taking place in the cells. The method further includes applying the lysate to an immobilized series of binding reagents which can discriminate the pathway molecules and their states. Binding events between the pathway molecules and the binding reagents are identified and the state of the selected signal pathway is determined.

8 Claims, 20 Drawing Sheets

(56) References Cited

OTHER PUBLICATIONS

Gilbert, "Developmental Biology", 6th editiion, Sunderland (MA): Sinauer Associates, 2000. Excerpt available at http://www.ncbi.nlm.nih.gov/books/NBK/0043.*

Cooper, "The Cell: A Molecular Approach", 2nd edition, Sunderland (MA): Sinauer Associates, 2000. Excerpt available at http://www.ncbi.nlm.nih.gov/books/NBK/9870.*

Kholodenko et al, "Quantification of Short Term Signaling by the Epidermal Growth Factor Receptor", The Journal of Biological Chemistry, Oct. 15, 1999, vol. 274, No. 42, pp. 30169-30181.*

* cited by examiner

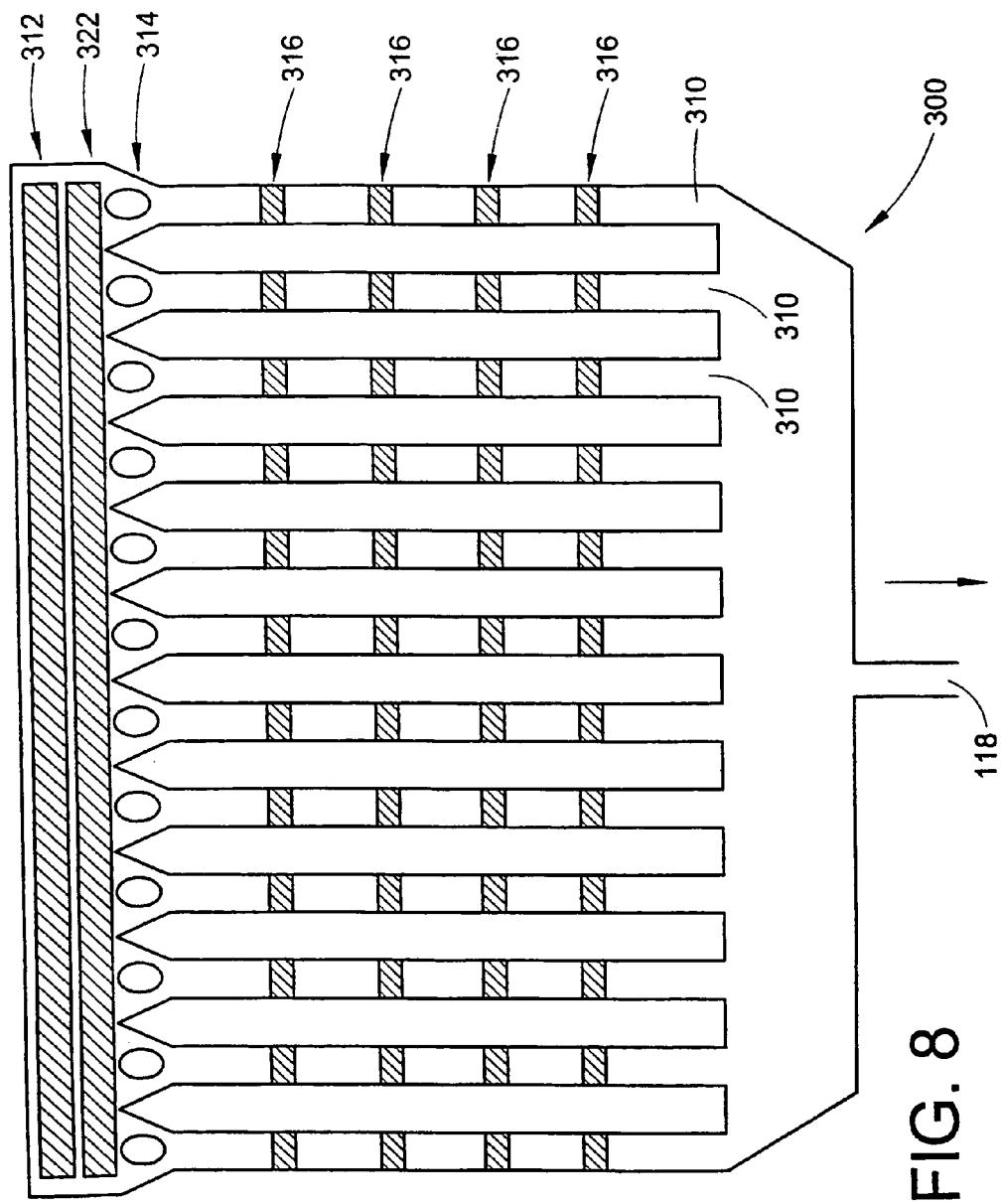

α - INTERFERON TREATMENT
SAMPLE: PERIPHERAL BLOOD LEUKOCYTES
PRIMARY ANTIBODY / PROBE: p-STAT1

| | 0 MINUTE | 3 MINUTES | 10 MINUTES | 30 MINUTES |
|---|---|---|---|---|

Stat2

Stat1

| cts/s | | | | |
|---|---|---|---|---|
| Stat2 | 0 | 169.4 | 141.7 | 49.4 |
| Stat1 | 0 | 83.9 | 118.2 | 61.7 |

CPG BEADS CONJUGATED TO HRP
SUBSTRATE: SUPERSIGNAL

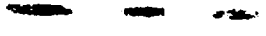 LIGHT OUTPUT ZONES SEPARATED
BY UNMODIFIED CPG BEADS
1 SECOND / HIGH RESOLUTION PACKED COLUMN

 LIGHT OUTPUT OF "PLUG FORMAT"
1 SECOND / HIGH RESOLUTION

 PHOTO OF ZONES SEPARATED BY PLUGS

 OVERLAY OF "PLUG FORMAT"

FIG. 13A

CPG BEADS CONJUGATED TO P14-Thy
CONJUGATE: P3-AP (1:500)
SUBSTRATE: DuoLux-AP

 LIGHT OUTPUT 1 SECOND / HIGH RESOLUTION

 PHOTO OF DRUMMOND CAPILLARY

 OVERLAY

FIG. 13B

CPG BEADS CONJUGATED TO P14-Thy
CONJUGATE: P3-HRP (1:1000)
SUBSTRATE: DuoLux-AP

 LIGHT OUTPUT 1 SECOND / HIGH RESOLUTION

 PHOTO OF DRUMMOND CAPILLARY

 OVERLAY

FIG. 13C

SENSITIVITY OF CPG BEADS
CTS/S    BACKGROUND          1 HRP CPG BEAD
            423                         1424
FIG. 14A
SPECIFICITY OF BINDING TO CPG BEADS
SAMPLE: 10ug/mL p-STAT1 PEPTIDE: BSA
PROBE: p-Tyr (RC20): AP
           STAT 1       p-STAT 1
CTS/S    15905        18430
PEPTIDE DISPLACEMENT STUDY
p-STAT 1 CPG BEADS
BLOCKING PEPTIDE: 10ug/mL p-STAT 1 PEPTIDE: BSA
PROBE: p-STAT 1 PEPTIDE: HRP
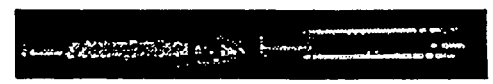
        -PEPTIDE     +PEPTIDE
CTS/S    16200       10099    CORRECTED
FIG. 14B STAT 1 CPG BEADS
SAMPLE: INF-ALPHA TREATED PBL'S (50uL)
PROBE: p-TYR(RC20): AP
SUBSTRATE CDP-STAR
JUNIOR DATA
| | |
|---|---:|
| NEGATIVE | 36571 |
| 7 MIN RE-RUN | 39712 |
| BEAD WASH | 4857 |
| POSITIVE | 34100 |
| 7 MIN RE-RUN | 409185 |
NIGHT OWL DATA
NEGATIVE 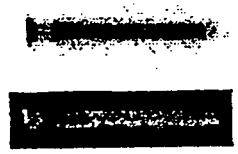 135 CTS/S
POSITIVE 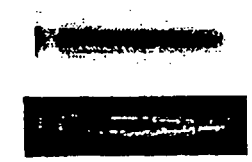 313 CTS/S
FIG. 16

CPG STAT1 ANTIBODY BEADS
PRIMARY ANTIBODY: p-Tyr
SECONDARY ANTIBODY: GAM-AP
SAMPLE: INTERFERON ALPHA TREATED PBL's
NEGATIVE
POSITIVE
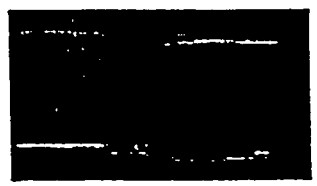
NEGATIVE 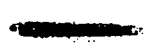 572 cts/s
POSITIVE 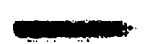 1202 cts/s
FIG. 17

CPG STAT 1 ANTIBODY BEADS IN Z-SPIN COLUMNS
PRIMARY ANTIBODY: p-TYR
SECONDARY ANTIBODY: GAM-AP
SUBSTRATE: CDP-STAR
SAMPLE: PERVANADATE TREATED PBL'S
CYS/S      6832      9610
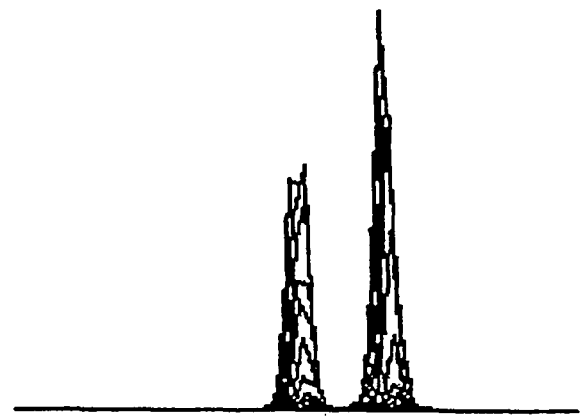
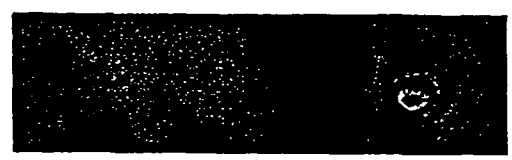
NEUTRAVIDIN BEADS      STAT 1 AB BEADS
FIG. 18

METHOD AND APPARATUS FOR SIGNAL TRANSDUCTION PATHWAY PROFILING

RELATED APPLICATION

This application claims the benefit under 35 U.S.C. §119 (e) of U.S. provisional application Ser. No. 60/179,997, filed Feb. 3, 2000. U.S. provisional application Ser. No. 60/179,997 is incorporated herein by reference in its entirety.

BACKGROUND OF THE INVENTION

The present invention relates to an apparatus and method for assessing the status of a cellular pathway. Several biotechnology companies are developing DNA-chips which contain printed arrays of hundreds or thousands of genes, or more. However, the DNA sequence of the genes or the level of gene expression do not reflect the actual functional state of the proteins encoded by the genes. The functional state of each protein involves more than simply the amount of the proteins. It includes, for example, post translational modifications (phosphorylation, glycosylation, etc.), binding partners in cellular pathways, conformation, enzymatic function, and state of activation. Moreover, each cell in the body has a pattern of functional proteins which reflects the current biologic working state of the cell (e.g., growing, differentiating, diseased, dying, senescent, etc.). Therefore, there exists a need in the art for a device and method for determining the status of cellular pathways (e.g., the phosphorylation state or binding partners of involved proteins) in tissue samples, including human tissue samples, thus providing the diagnostician or clinician with an early warning of impending or occult toxicity, disease state, response to treatment, differentiated function, and so forth.

SUMMARY OF THE INVENTION

The present invention provides a molecular detection device having a plurality of binding or reaction sites comprising a series of immobilized recognition molecules or binding reagents selected and arranged to qualitatively or quantitatively assess the status of a series of signal transduction pathway proteins or other protein-protein interactive network, their phosphorylated or activated state, and their binding partners, in a cell sample to determine the status of a selected cellular signal transduction pathway. Knowledge of the pathway status can then be used by the diagnostician or clinician to determine the health of the sampled cells, drug or other treatment efficacy or toxicity. This knowledge can also be used to identify candidates for selected therapies, to aid in therapy selection for a given subject, and to determine drug toxicities.

Protein interactions are defined herein as the coupling of two or more proteins in a given space and time such that a binding reaction occurs, and/or one protein modifies the other protein. The novel concept of the invention is that the protein networks and pathways, and their changing state in cells, can be recapitulated after the cells are dissolved and the proteins are solubilized. The invention method recapitulates the proteins involved in networks because a) networks are built from proteins binding to other proteins to form larger complexes; and b) phosphorylation events cause specific proteins to interact with (or dissociate from) other proteins in a certain order. Therefore, the upstream and downstream networks emanating from any given point can be elucidated by using the subject invention to find at least two proteins that are phosphorylated and forming complexes with other proteins. This pattern changes with disease state or drug treatment or toxicity.

In a preferred embodiment, multiple nodes in a signal transduction pathway circuit within a cell are profiled to determine whether the entire pathway is functionally activated and in use by the cell or whether only a portion of the pathway is activated (e.g., upstream or downstream), thus indicating, for example, that the pathway may be regulated at intermediate points along the pathway circuit. Also, the binding partners which complex with individual nodes of the pathway can be identified.

In still a further aspect, a method of identifying the full repertoire of proteins that could serve as acceptors for phosphorylation comprises treating cells, such as whole tissue specimens grown ex-vivo, or animal tissue treated in vivo with compounds that inhibit protein tyrosine and/or serine/threonine phosphatase activity such as sodium pervanadate, okadaic acid, calyculin A, for acute periods of time (e.g., less than 3 hours), and isolating the cells of interest. The cells of interest are lysed and selected for the phosphorylated proteins using antibodies on an immobilized bait, such as anti-phosphotyrosine, anti-phosphoserine, and/or anti-phosphothreonine antibodies, and so forth. The phosphoproteins in the enriched fraction are separated, e.g., by chromatographic and/or electrophoretic means and the primary amino acid sequence of the proteins is identified by enzymatic digestion or chemically-induced protein fragmentation followed by standard mass spectrometric techniques. Finally, antibodies or binding molecules that specifically bind to the identified proteins are developed.

In further embodiments, protein pathways which reflect a disease state can be fingerprinted to pinpoint a therapeutic target. In order to select a treatment or determine treatment efficacy, informatics or heuristics can be developed for various pathways, pathological states, therapies, and the like.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 7 illustrates a system and method for identifying therapeutic targets employing trapped lysates from cells of different pathological states.

FIG. 8 shows a multiplexed embodiment of the molecular detection device in accordance with the present invention.

FIGS. 13A-13C, 14A, 14B, and 15-18 illustrate the use of activated glass beads as the flow-through matrix of the present invention.

DETAILED DESCRIPTION OF THE PREFERRED EMBODIMENTS

Figure 1:
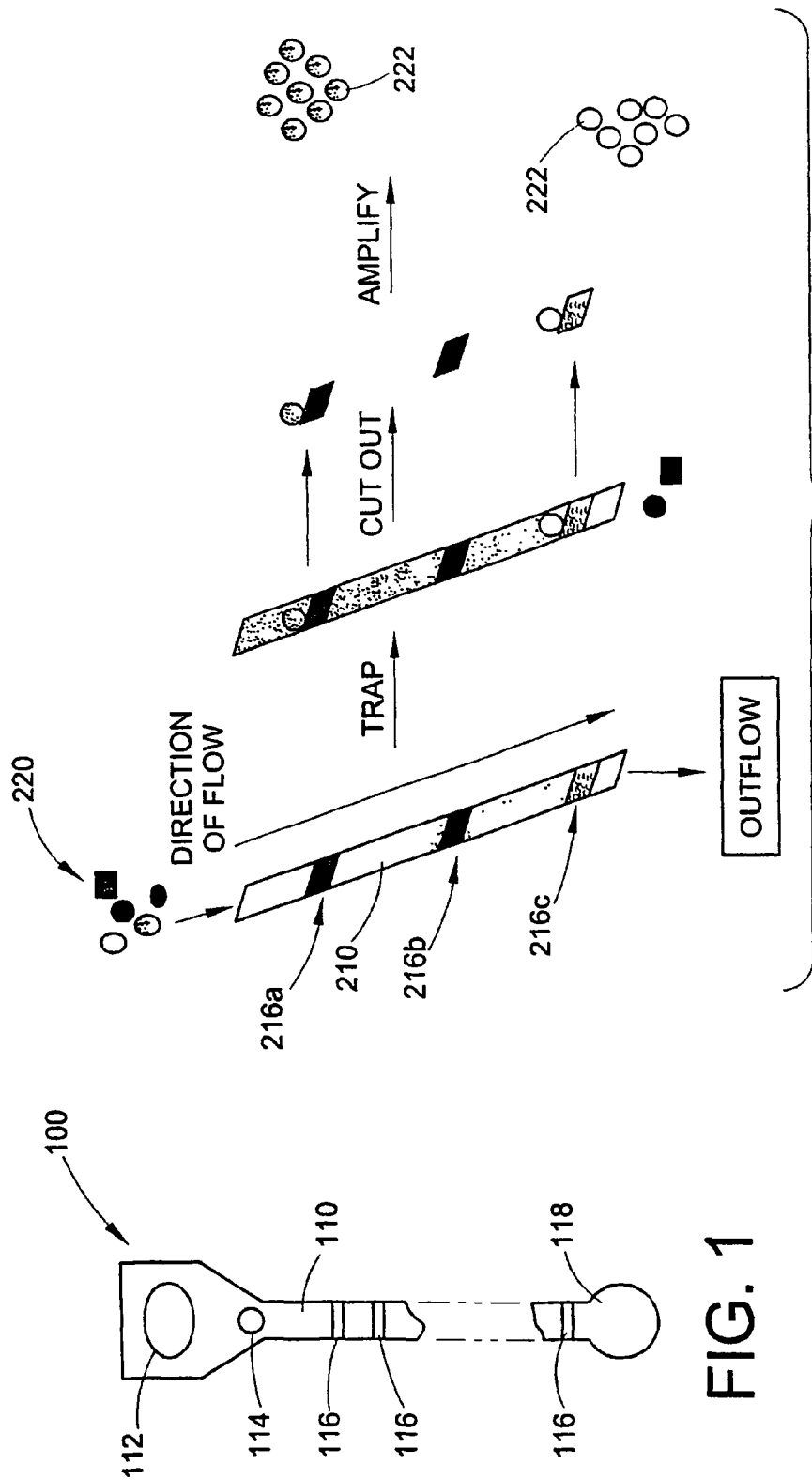
FIG. 1 illustrates a cellular signal transduction pathway profiling device of the present invention.
Figure 2:
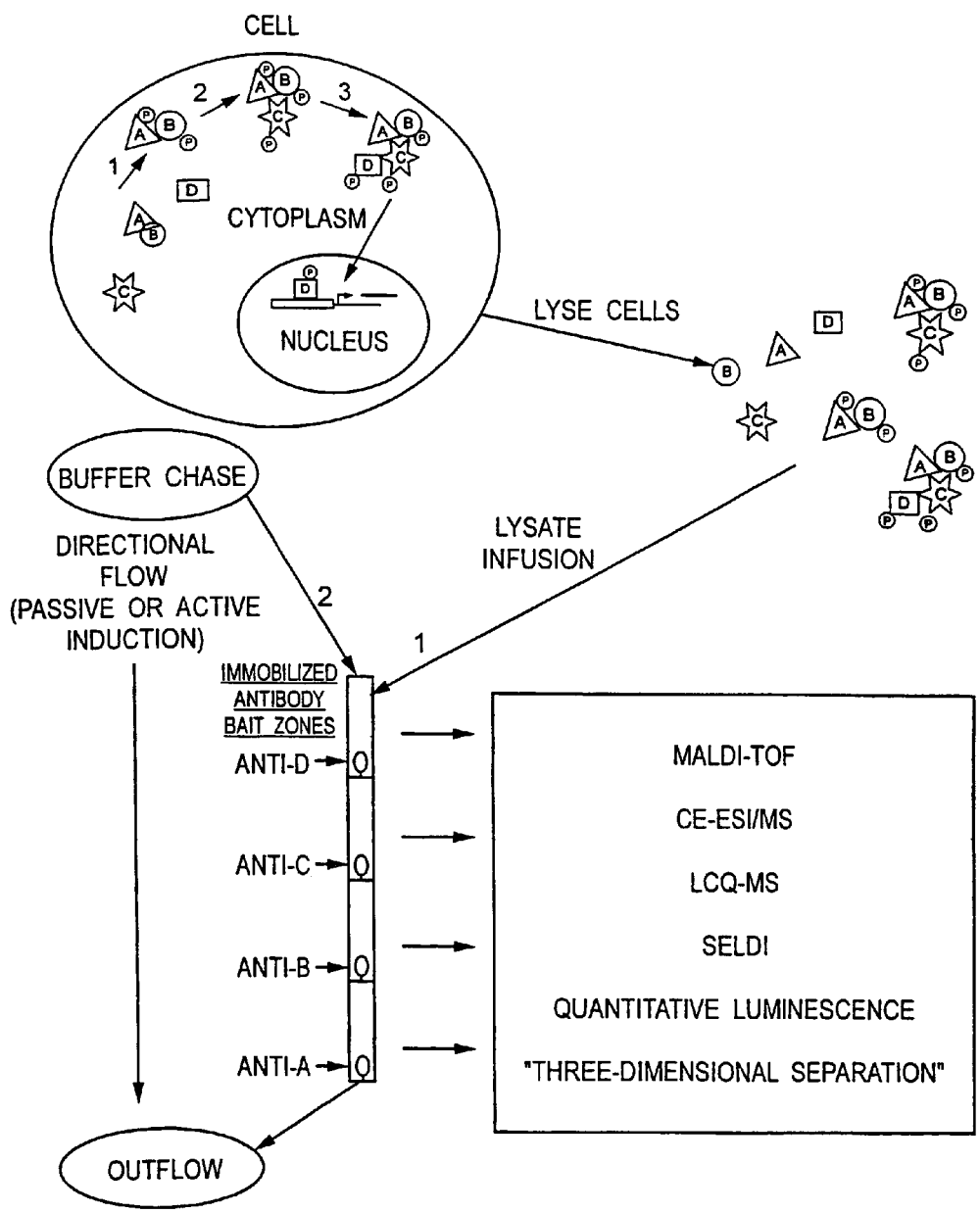
FIGS. 2-6 illustrate exemplary pathway profiling methods in accordance with the present invention.
Figure 3:
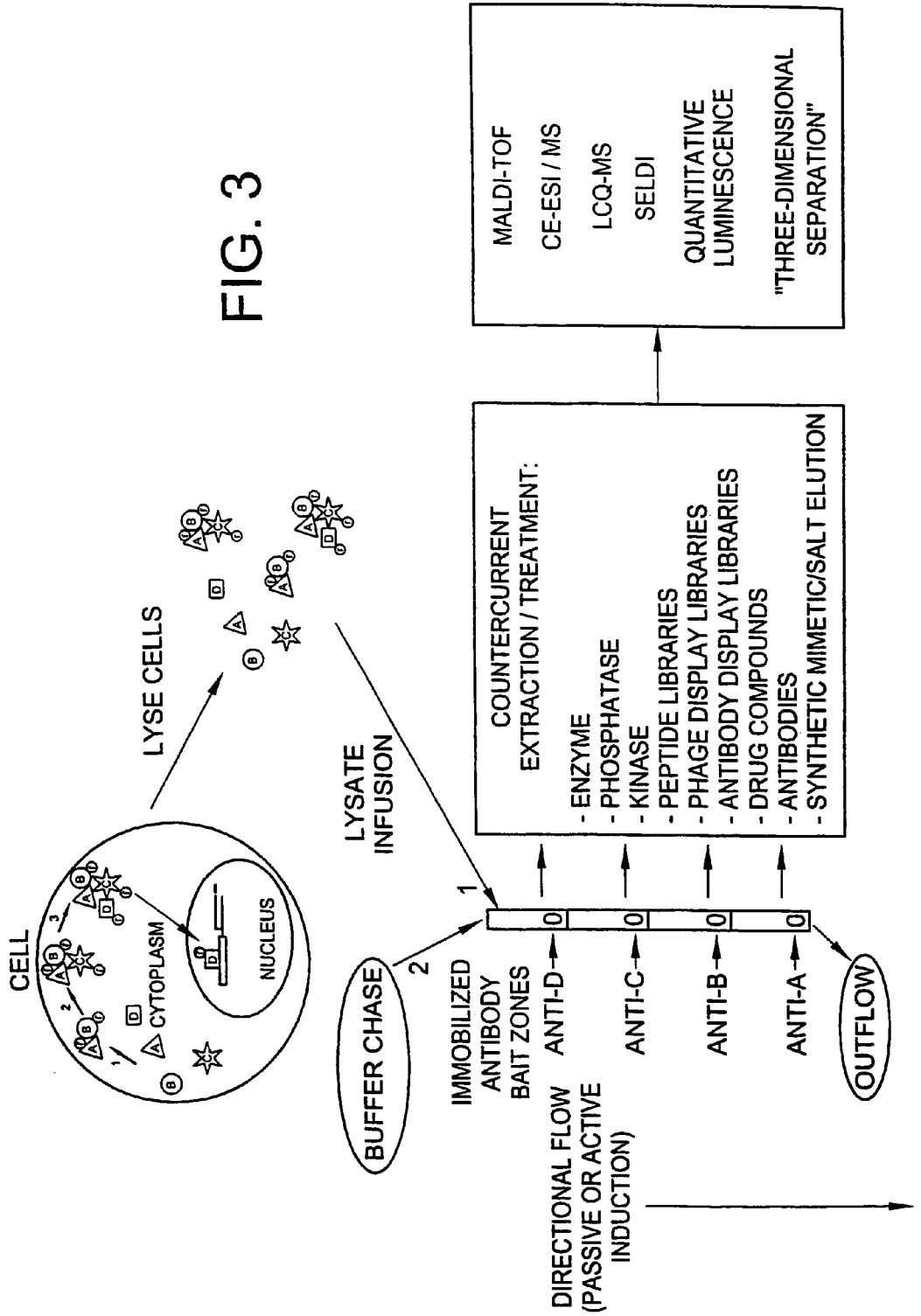
Figure 4:
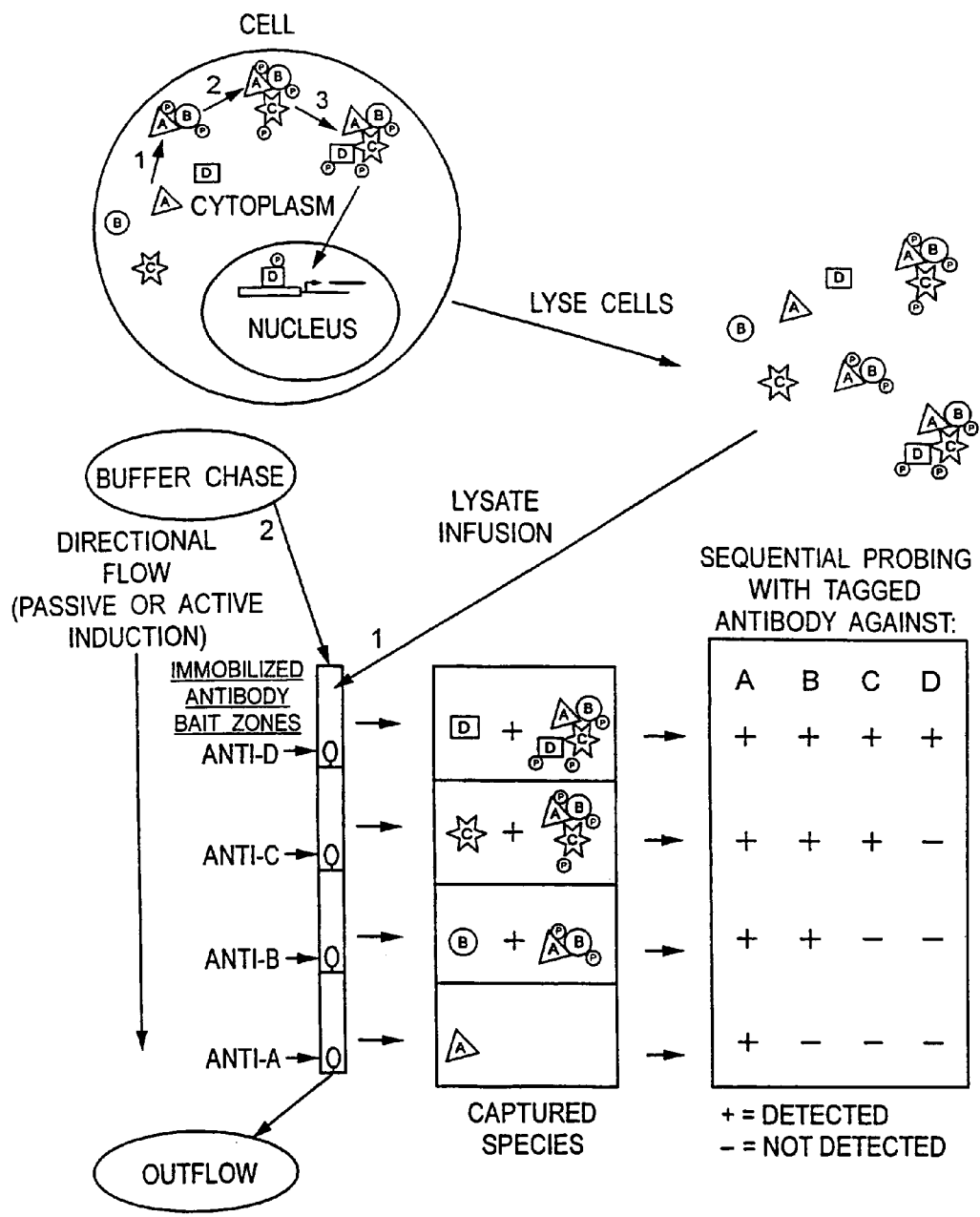
Figure 5:
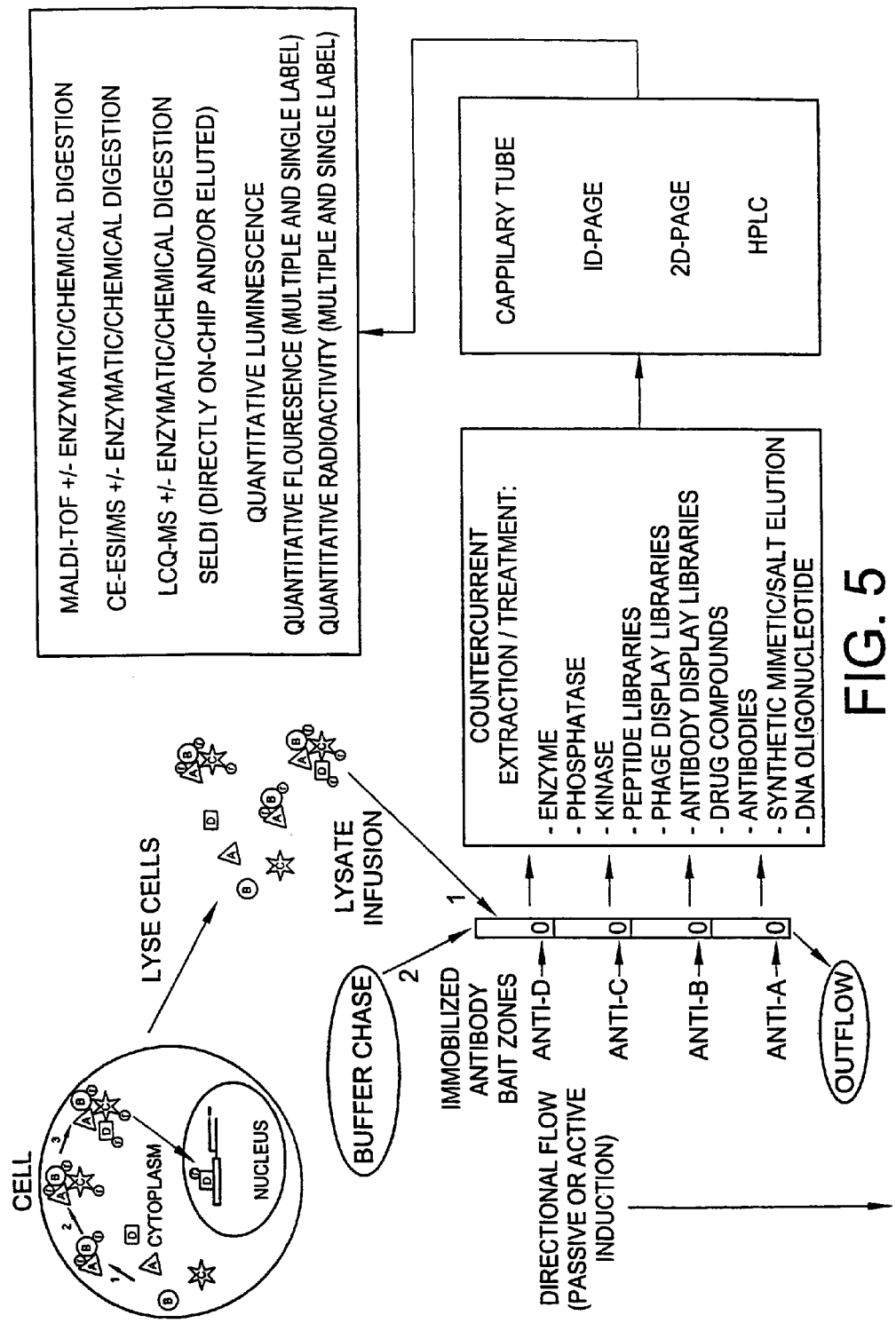
Figure 6:
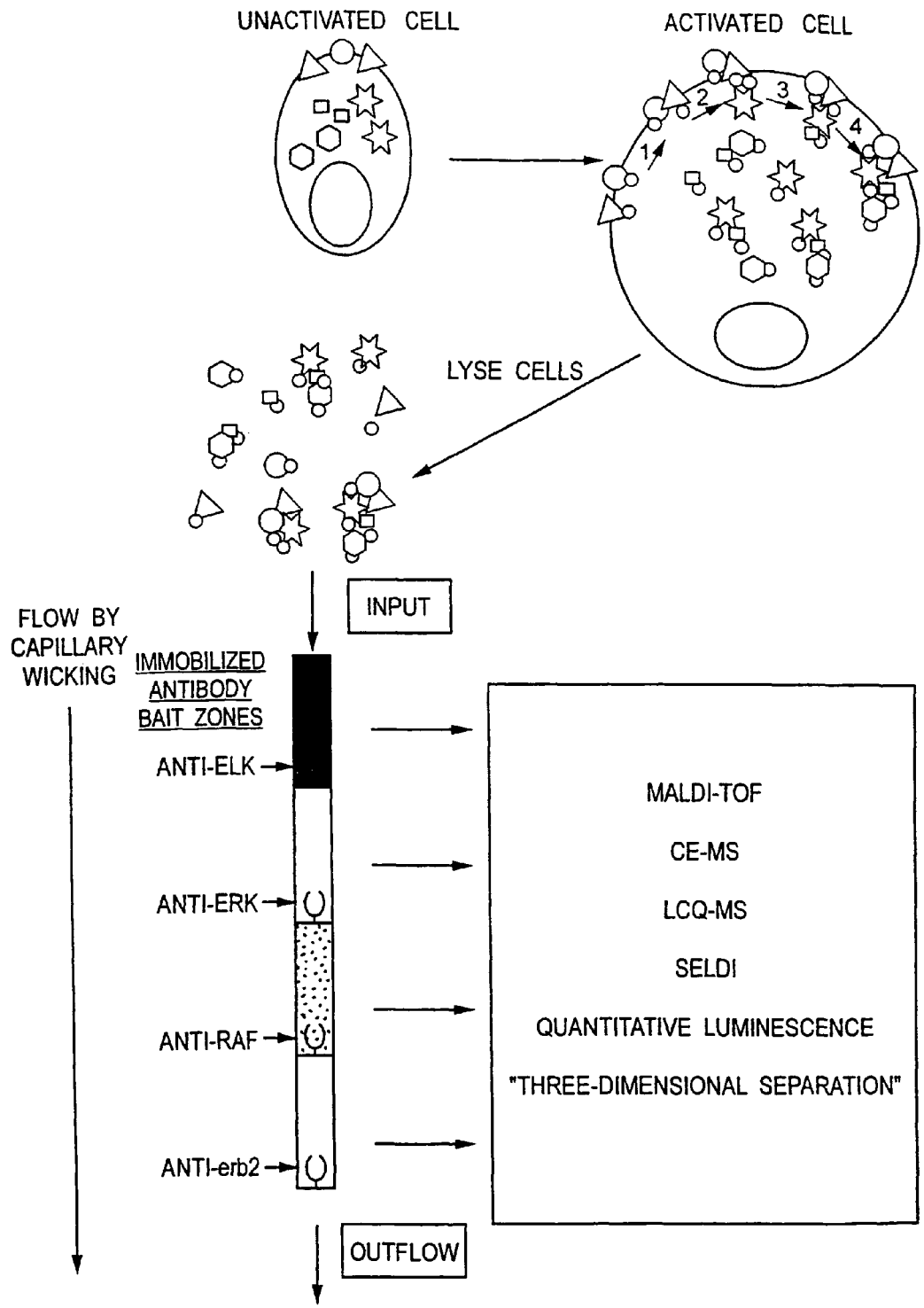

Referring now to FIG. 1, a cellular signal transduction pathway profiling device 100 includes a porous support member 110, such as a porous membrane or the like. Support member 110 may be fabricated from any material into which fluids may flow and readily pass through, such as nitrocellulose, cellulose, glass, nylon, or other fibrous material. On the support 110, two or more, preferably three or more, distinct binding site regions or trapping zones 116 are formed by applying and immobilizing within each region a substance capable of reaction with an analyte contained within the test sample. In a preferred embodiment, each region contains a single purified ligand, such as a protein, peptide, antibody, or drug capable of trapping a specific protein or modification thereof involved in a selected transduction pathway. Alternately, the immobilized materials at the binding sites are complex mixtures (e.g., cellular lysates). By "immobilized" is meant that the substance capable of holding an analyte is applied in a confined area on the surface of the membrane such that it is permanently bound or otherwise incapable of substantial movement to positions elsewhere on the support.

A lysate application region 114 and a chase application region 112 are provided at one end of the device 100. In this manner the lysate can be applied to the support 110, followed by a chase, such as a buffer or other physiological solution, to cause the lysate to flow through the trapping zones 116 to an outflow region 118. Preferably, the lysate is drawn through the reaction zones via wicking or capillary action, although other methods are contemplated as well, such as gravity, application of a pressure differential, electrical pumping, and so forth. The trapping zones are applied in a manner such that subsequent capillary wicking of material for analysis will pass through the immobilized protein zone and not around it. In one embodiment, the support material 110 forms a strip and the reaction zones 116 are applied in a line traversing the width of the strip.

When antibodies are used for trapping, they may be from any species, including but not limited to human, goat, rabbit, mouse, etc. The antibodies can be either anti-protein specific (e.g., anti-ERK kinase) or anti-modified protein specific (e.g., anti-phosphorylated ERK kinase).

For signal transduction profiling, the sequence of the applied antibodies in the multiple reaction zones 116 are preferably ordered such that the protein components of a pathway that are activated last are captured first, although the ordering is otherwise not necessarily critical. For example, the analysis of EGF signaling profiles from cells that are expressing differential amount of the erb receptor family can be analyzed by imprinting antibodies recognizing the phosphorylated forms of proteins in the EGF receptor signaling cascade. The order of imprinting, from first capture zone to last capture zone, is shown below in TABLE 1.

TABLE 1

| Capture Zone | Antibody |
| --- | --- |
| 1 | anti-phosphorylated c-myc |
| 2 | anti-phosphorylated c-jun |
| 3 | anti-phosphorylated p70RSK |
| 4 | anti-phosphorylated erk |
| 5 | anti-phosphorylated AKT |
| 6 | anti-phosphorylated c-RAF |
| 7 | anti-phosphorylated erb2 |
| 8 | anti-phosphorylated erb1 |

Once the trapping zones 116 have been imprinted on the support 110, cellular lysates, DNA aptomer libraries, focussed or unfocussed drug libraries, and/or phage display libraries, can be applied to the top of the detection device 100 in the defined application zone 114 and allowed to actively wick through the support 110 by active capillary action using a buffer chase applied to region 112. Again, other methods of drawing the lysate through the zones 116 are also contemplated.

Analytes in the material for analysis, such as proteins, drugs, DNA, phages, will, depending on their abundance, specifically bind to a corresponding trapping zone region 116 having a substance capable of reaction therewith. All other components will wick through the zone into the waste outlet region 118 at the bottom of the chip 100.

Because these analyses are performed under native conditions, protein complexes, comprising activated proteins (e.g., phosphorylated proteins) and their binding partners will be trapped in each of the subsequent zones, depending on the degree of phosphorylation and the presence of the binding partners.

Subsequent analysis and/or identification of proteins trapped in the zones 116 is performed by countercurrent extraction, treatment with enzymes (e.g., trypsin), mimetics (e.g., phenylphosphate for the removal of phosphotyrosine-containing proteins), and so forth. Analysis of extracted material can be performed by elution into other trap zones (three-dimensional separation) or by mass spectrometry (e.g., LCQ-MS, CE-ESI-MS) for identification and discovery purposes. Additionally, quantitative analysis of trapped analyte composition can be performed by querying each trap zone with a tagged or detectably labeled antibody (e.g., biotinylated or alkaline phosphatase tagged) to generate a signal. Exemplary methods for detecting the bound proteins are illustrated in FIGS. 2-6.

An exemplary embodiment in which each trapping zone 116 is imprinted with lysates from cells of different types or different pathological states is illustrated in FIG. 7. Phage and/or DNA aptamer libraries 220, such as random phage and/or random aptamer libraries, can be screened and analyzed by successive rounds of trapping with a plurality of protein lysate zones 216a-216c. For example, in a first binding site 216a, there is applied and immobilized a normal cell lysate. In a second binding site 216b, there is applied and immobilized a lysate of cells in a predisease state. In a third binding site 216c, there is applied and immobilized a lysate of diseased cells. Each round of trapping is followed by amplification. For example, each binding site can be cut out and amplified using PCR (for aptomer libraries) or amplification by infection (e.g., in E. coli for phage display peptide libraries). Alternately, small molecule drugs can be identified by NMR or other like methodologies. The amplified entities 222 can then be used for potential targeting therapies, e.g., as toxin-conjugated vehicles. For example, an amplified entity which selectively binds to a protein representative of a disease state, such as cancer, can be conjugated or linked to a toxin for efficient delivery of the vehicle to the targeted cells. Likewise, an amplified entity can be conjugated to an imaging reagent for diagnostic imaging of the targeted cells, such as x-ray contrast agents, MRI contrast agents, radiopharmaceuticals for nuclear medicine diagnostic imaging, and so forth. These entities can be further screened for DNA or peptide sequences that bind to unique cell-specific or tissue-specific proteins by repanning against immobilized bait trap surfaces.

Referring now to FIG. 8, there is shown another embodiment of the present invention in which a molecular detection device 300 comprises a plurality of support members 310 arranged in a multiplexed format. Each support member includes a plurality of binding sites 316 to which is applied and immobilized a series of proteins and modifications thereof involved in a selected signal transduction pathway. Such a format is suitable for high-throughput drug screening using cell lines and/or microdissected tissue cell lysates. A lysate application zone 314 is provided for each strip 310. In alternate embodiments, the zones 314 are cell growth zones for selected cell lines, in which case an optional lysing buffer application zone 322 is provided such that the cells are lysed prior to reaching the trapping zones 316. A chase application zone 312 is provided for application of a buffer or other physiological solution to carry the lysate through the trapping regions 316. Analytes in the lysate will specifically bind to a corresponding trapping zone region 316 having a substance capable of reaction therewith and all other components will wick or otherwise be drawn through the zones into the waste outlet region 118 at the bottom of the device 300.

Figure 9:
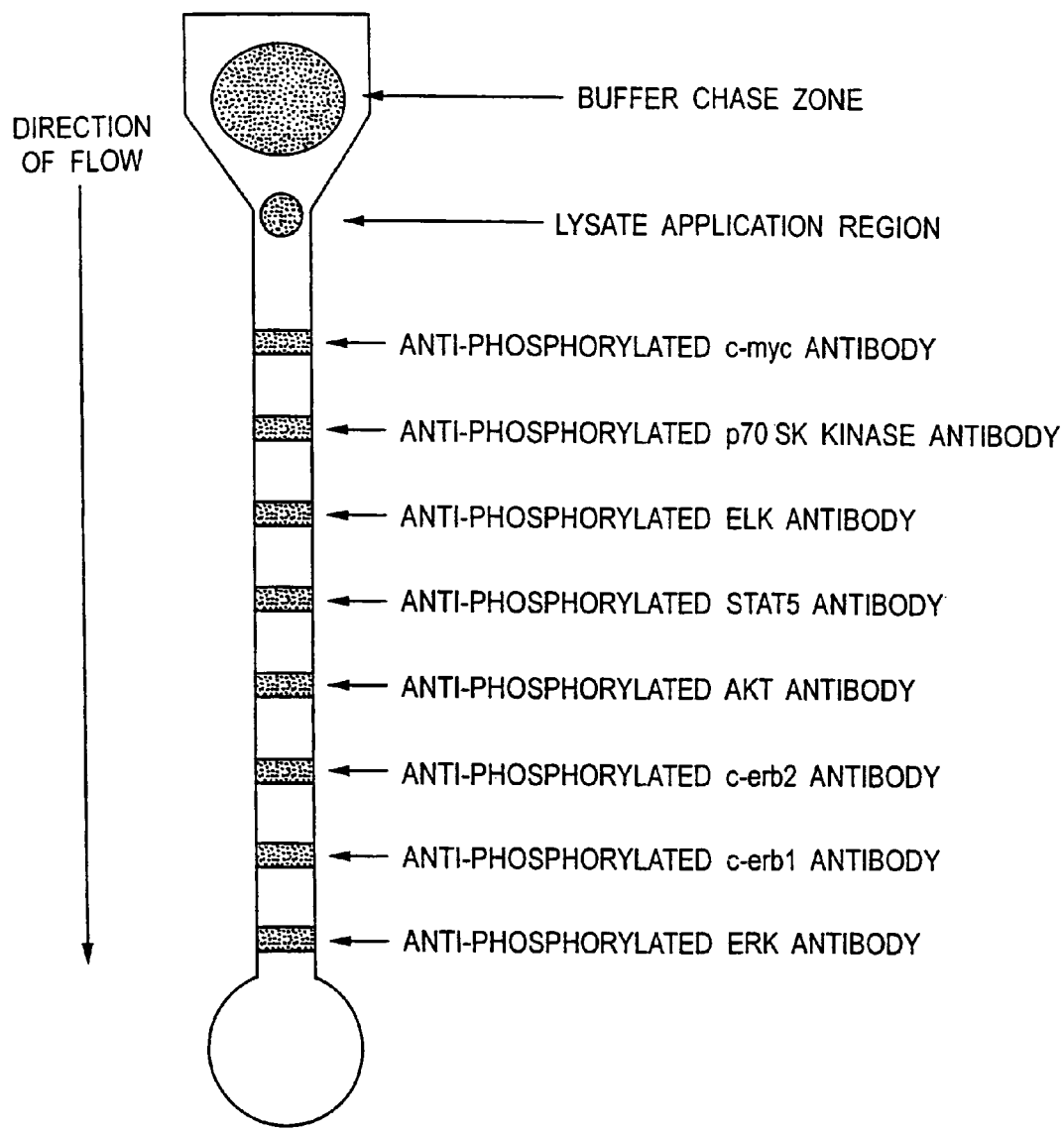
FIG. 9 illustrates an exemplary pathway profiling device according to the present invention.

The reduction of this method to practice has been demostrated in the following tests. A pure nitrocellulose membrane (0.45 micron pore size, Shleister and Schuell) was cut as a 6 cm×1 strip beginning and ending with wider 3 cm×3 ends. The following commercially available rabbit polyclonal antibodies (New England Biolabs, Upstate Biotechnology) at 100 microgram/ml concentration were applied undiluted in total applied volume of 2 microliters as traping zone "stripes" perpendicular to the length of the menbrane as shown in FIG. 9. The antibodies were applied in bands approximately 2-3 mm wide, spaced at repeated 0.5 cm intevals, and ordered from top to bottom as shown in TABLE 2.

TABLE 2

| Capture Zone | Antibody |
| --- | --- |
| 1 | anti-phosphorylated c-myc |
| 2 | anti-phosphorylated p70 SK kinase |
| 3 | anti-phosphorylated elk |
| 4 | anti-phosphorylated STAT5 |
| 5 | anti-phosphorylated AKT |
| 6 | anti-phosphorylated c-erb2 |
| 7 | anti-phosphorylated c-erb1 |
| 8 | anti-phosphorylated erk kinase |

The antibodies were allowed to bind to the membrane overnight, after which the entire strip was immersed in a commercially available casein blocking solution (Superblock, Pierce Chemical) for 2 hours. The membrane was then washed 3 times for 10 minutes with 20 milliliters of a 50 mM TRIS, 100 mM NaCl, 0.5% Tween-20 solution (TBST). The strip was then allowed to air-dry for 5 hours.

Lysates comprised of 1500 cells procured via Laser Capture microdissection (LCM) of two human breast cancer specimens, one known to be highly reactive for erb2 (erb2+), and the other known to be weakly reactive (erb2−), were applied to the top of the strip (lysate application region) in a volume of 5 microliters of commercially available lysing buffer (T-PER, Pierce Chemical) with a commercially available protease inhibitor cocktail (Complete Tablets, Boehringer Mannheim) and 1 µl sodium vanadate as a phosphotyrosine phosphatase inhibitor. 25 microliters of the T-PER solution was applied as a chase immediately after the application of the lysate, and the lysates were allowed to actively "wick" through the strip over a period of 60 minutes. An additional volume of 25 microliters of T-PER was applied to the chase zone when the buffer front was approximately ½ of the way through the strip.

Five minutes after the buffer front had passed through the last antibody trap zone, the entire strip was immersed and washed 3 times for 10 minutes in TBST. The strip was then immersed in TBST+ mouse monoclonal anti-ERK (Transduction Laboratories) at a 1:2000 dilution for 1 hour. The strip was then washed 3 times for 10 minutes each time with TBST, and then incubated for 1 hour with a biotinylated goat anti-mouse IgG antibody (Vector Laboratories) at a 1:5000 dilution.

Figure 10:
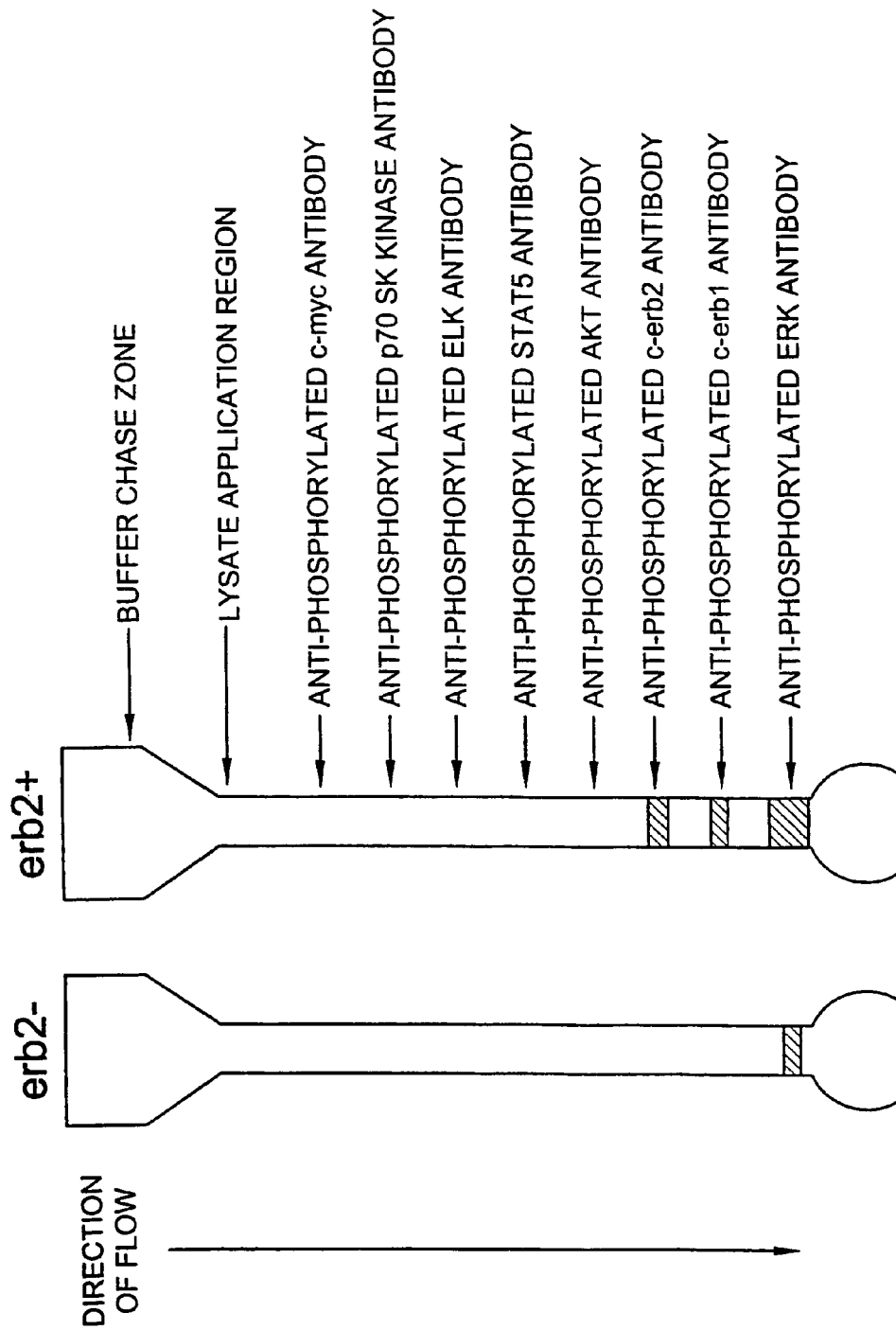
FIG. 10 illustrates autoradiography results for microdissected erb2+ and erb2− human breast cancer epithelium from tissue sample specimens probed for anti-ERK1/2 mouse monoclonal antibody using the pathway profiling device according to FIG. 9.

The strip was then washed 3 times for 10 minutes each time in TBST, and developed according to the package insert from Vector Laboratories using a commercially available kit (ABC reagent) which generates luminescent output. The strips were then exposed to standard autoradiography for 1 second to 30 second exposures. The results of the autoradiography are illustrated in FIG. 10.

The following experimental example demonstrates the recapitulation of the state of a cellular signal pathway using proteins dissociated from lysed human cells treated with a drug known to activate the selected signal pathway.

The Janus kinase-signal transducer and activator of transcription (JAK-STAT) signaling pathway is important in the Interferon Alpha (IFNA) cellular response. Binding of IFNA induces the following sequence of events:
Fusion of Interferon Alpha Receptor (IFNAR)1 and IFNAR2;
Jak1 and Tyk2 are phosphorylated;
IFNAR1 is phosphorylated allowing docking of Stat2;
Stat2 is phosphorylated allowing Stat1 to dock;
Stat1 is phosphorylated;
Stat1(Pi)-Stat2(Pi) heterodimer is released.

Interferon Alpha Treatment of Peripheral Blood Lymphocytes

Peripheral Blood Lymphocytes (PBLs) were isolated using Histopaque-1077 (Sigma). The PBLs were suspended in PBS (0.01 M phosphate buffered saline, 0.138 M NaCl, 0.0027 M KCl), pH 7.4, and allowed to acquiesce overnight at 4° C. The cells were pelleted by centrifugation at 5000×g for 5 minutes. The supernatant was decanted off, and the cells resuspended in RPMI-1640 media (Bio-Whittaker) at approximately 20 million cells/mL. The cells were treated with 13,500 units/mL of recombinant human interferon alpha (BioSource) for 0, 3, 10 or 30 minutes. Once the incubation was complete, cells were pelleted by centrifugation at 5000×g for 5 minutes. Cells were washed with ice-cold PBS and resuspended in lysis buffer ((T-PER, Pierce), 10 mM beta-glycerophosphate, 1 mM sodium molybdate, 2 mM sodium orthovanadate, 2.5 mM AEBSF and 5% glycerol). The cells were vortexed and placed on ice for 5 minutes, repeated. Lysates were clarified by centrifugation at 10,000×g for 5 minutes. The supernatant was snap frozen and stored at −80° C.

Pervanadate Treatment of Peripheral Blood Lymphocytes

Peripheral Blood Lymphocytes (PBLs) were isolated using Histopaque-1077. The PBLs were suspended in PBS and allowed to acquiesce overnight at 4° C. The cells were pelleted by centrifugation at 5000×g for 5 minutes. The supernatant was decanted off, and the cells resuspended in RPMI-1640 media at approximately 20 million cells/mL. A pervanadate solution was made as follows. 882 µL of 0.10 M sodium orthovanadate was added to a mixture containing 832 µL RMPI-1640 media and 50 µL 30% $H_2O_2$, mixed at room temperature, and let stand for 15 minutes. The cells were treated with pervanadate 1 µL to 500 µL of cells for 30 minutes at 37° C. Cells were pelleted at 5700×g for 5 minutes. Pellets were washed with ice-cold PBS and snap frozen. T-PER (salt concentration was adjusted from 0.150 M to 0.20 M) was added to the pellet and the resulting lysate was vortexed rapidly for 1 minute. The lysate was clarified by centrifugation at 15,000×g for 10 minutes. The supernatant was snap frozen and stored at −80° C.

Preparation of Flow-Through Trapping Zones

FF85 (Schleicher and Schuell) nitrocellulose membranes were cut into approximately 8 cm×1 cm strips. Stat2 antibody (C-20, Santa Cruz Biotechnology) was spotted down at 0.5 µL increments/2.5 µL total across the 1 cm width of the strip at approximately 6.0 cm from the top. Stat1αp91 antibody (C-24, Santa Cruz Biotechnology) was strided down at 0.5 µL increments/2.5 µL total across the 1 cm width of the strip at approximately 7.0 cm from the top. The treated membranes were dried for 45 minutes at room temperature and 6% relative humidity. The strips were blocked in Superblock (Pierce Chemical Company) for 3 hours at room temperature with shaking. The strips were washed 3 times with TBS-T (0.20 M Tris, 0.50 M NaCl, 0.1% Tween20), pH7.5, then dried at 37° C./6% relative humidity.

p-Stat1 Association Strip Assay

Figure 11:
FIG. 11 illustrates a method of the present invention for the detection of IFNA stimulation of the JAK-STAT signal pathway.

The IFNA treated PBL lysates (25 µL) were placed approximately 1 cm from the top of the strip. The lysate was moved through the strip upon addition of TBS-T to the top of the strip. Every 20 minutes over a period of 3 hours, 50 µL of TBS-T was placed at the top of the strip. Upon completion the entire strip was washed 1 time with TBS-T. The strips were incubated overnight at 4° C. with p-Stat1 (A-2, Santa Cruz Biotechnology) diluted at an appropriate concentration in Superblock. The strips were washed 3 times with TBS-T. The strips were then incubated at room temperature for 3 hours with Goat Anti-Mouse:Alkaline Phosphatase (Fortran, In House Conjugation to AP) diluted in Superblock. The strips were washed 3 times with TBS-T. The strips were incubated with CDP-Star (Tropix) for 5 minutes. Light output/binding of p-Stat1 antibody was recorded using a CCD imager (NightOwl, Berthold Technologies). As shown in FIG. 11, the invention method was able to detect IFNA stimulation of the JAK-STAT signal pathway in the expected time-dependent manner.

CTNI Example

The following Example demonstrates how parallel arrays of flow-through binding zones useful for practicing the subject invention can be manufactured by using a laser engraver to build up porous matrix columns. The raised columns on a plastic backing contain and direct the flow of solubilized proteins to be analyzed. The example indicates the quantitative dose-dependent detection of troponin, an intracellular myofibril component of human cardiac muscle cells.

Nitrocellulose, purchased from Schleicher and Schuell, comprises an inert plastic (Mylar) backing support onto which a layer of directly cast nitrocellulose is deposited. During our investigation of this matrix for flow-through diagnostic applications, it was discovered that it is possible to create channels in the material. This was achieved by using the cutting power of a $CO_2$ laser. The laser is programmable through a computer software application, which enables the creation of highly complex patterns on the surface of the nitrocellulose. Briefly, the laser vaporizes the cellulose beneath the beam, exposing the underlying mylar surface. One of the simplest applications of this process is to take a 4 cm×4 cm square of nitrocellulose (or any other desired size) and use the laser to cut a series of vertical slots in the material. In this manner, one creates in the nitrocellulose a number of "columns", each column separated by an inert mylar barrier. Interpreted another way, a series of "usable" ridges are manufactured on the matrix, each ridge usable for a similar or dissimilar diagnostic application. The number of ridges created on the material varies with the width of the ridge and the length of the nitrocellulose piece. The laser action also scores the upper surface of the mylar, allowing for easy detachment of a single column or multiple columns from the sheet.

A series of columns (3 mm wide) were cut into a 4 cm×4 cm length of nitrocellulose. Seven columns were detached and treated as follows.

1 µl of a 1 mg/ml solution of neutravidin (Pierce Chemical Co., Rockford, Ill.) was applied to each ridge. The protein was heat (37*) cured on the matrix for 2 hrs. After washing, a 1 µl aliquot of biotinylated anti-cardiac troponin I antibody was overlayed onto the original neutravidin spot. Thirty minutes later, excess antibody was removed and the whole surface of the matrix blocked in a PEG/PVP solution.

A series of troponin I calibrators (purified from human heart muscle), ranging in concentration from 0 to 160 ng/ml were reacted individually with an anti-troponin I antibody conjugate. The latter recognizes a site on troponin I, which differs from the site recognized by the neutravidin bound antibody.

A 1 µl aliquot of each antigen/conjugate reaction was placed onto individual columns. The placement of the liquid was immediately below the neutravidin complex.

The lower edge of the seven column composite was placed into a buffer allowing the latter to move through the material via capillary action (conventional TLC). The length of time required for the buffer to reach the top of the device was 45 seconds.

The device was removed and coated in CDP* substrate (Tropix Corporation, Bedford, Mass.), light emission was recorded on a NightOwl CCD scanner of light emission.

Figure 12:
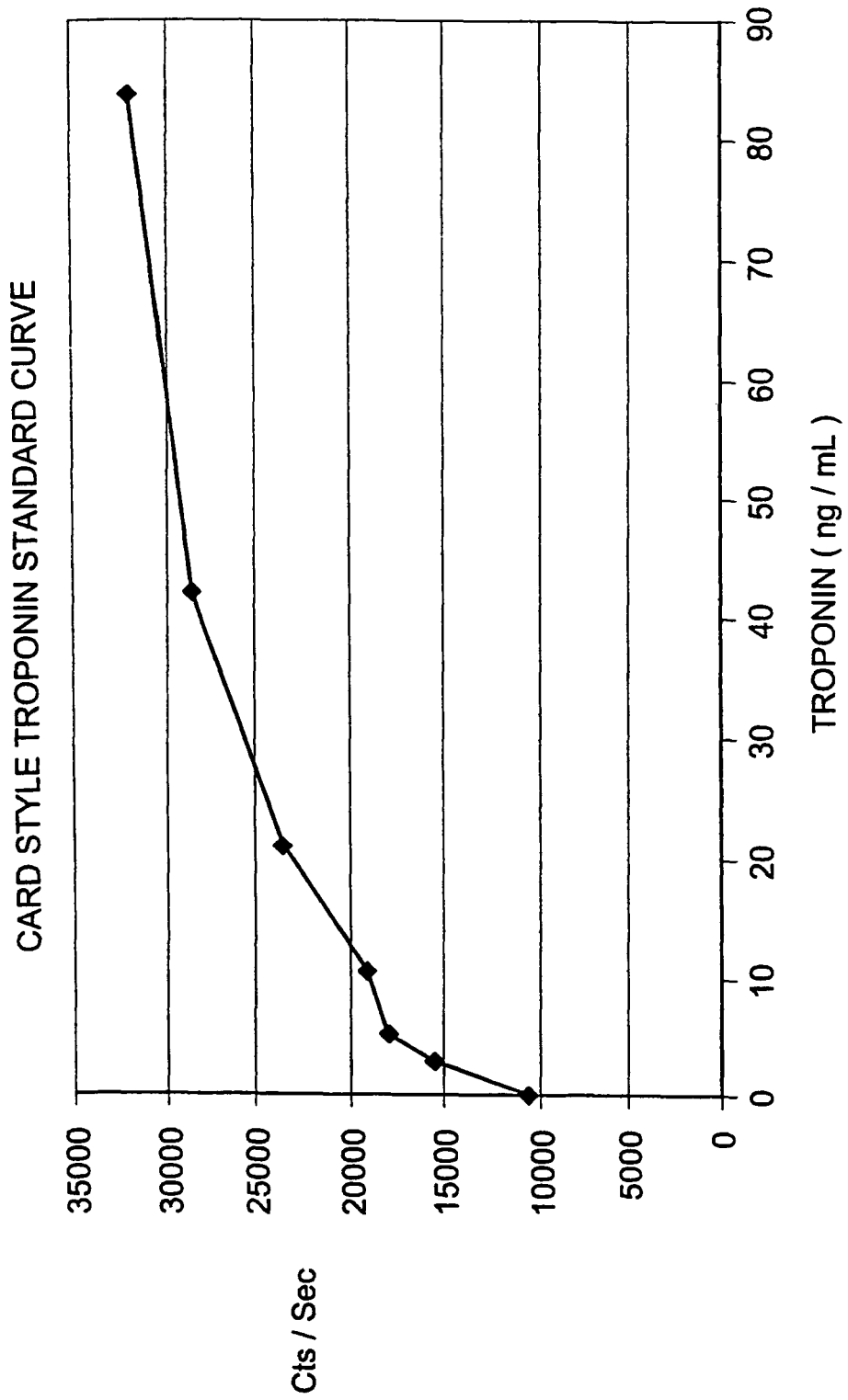
FIG. 12 illustrates the use of nitrocellulose engraved by a laser to manufacture raised porous columns that contain and channel the flow of cellular proteins through the zones. In the depicted example, a high sensitivity and dose dependence of protein detection is noted for the intracellular human heart muscle protein troponin.

The flow-through trapping zones created in nitrocellulose porous matrix columns efficiently retained antibody antigen complexes such that the troponin analyte could be measured in a dose-dependent manner as shown in FIG. 12 and TABLE 3.

TABLE 3

| Card Style Troponin Membrane; Dose Curve 1 µL(Sample + Conjugate) | |
|---|---|
| Troponin (ng/mL) | Light output (cts/sec) |
| 0 | 0 |
| 2.6 | 4955 |
| 5.2 | 7264 |
| 10.4 | 8477 |
| 20.8 | 13116 |

TABLE 3-continued

Card Style Troponin Membrane; Dose Curve 1
μL(Sample + Conjugate)

| Troponin (ng/mL) | Light output (cts/sec) |
|---|---|
| 41.65 | 18199 |
| 83.5 | 21415 |

The porous matrix material through which the cellular protein flows has been successfully reduced to practice with porous or fibrous materials, such as nylon, cellulose or silica, and can be configured as raised porous interconnecting columns or suitably packed particles or beads.

The following example demonstrated the use of activated glass beads to construct a flow through matrix of the present invention.

Controlled pore glass (CPG) is a matrix whose surface is readily modified by reaction with a wide variety of bifunctional silanes. The material exhibits a significant surface area to weight ratio. The rigid nature of the glass, high porosity and non-compressibility lends itself to rapid passage of liquids or biological fluids through the matrix. The present invention employing a series of capture zones having differing specificity for removal and quantitation of phosphorylated and non-phosphorylated protein complexes from stimulated cells can be achieved through the use of CPG.

By confining specific capture zones of CPG in a microcapillary tube, each zone separated by either inert glass or an inert cellulose plug, biological fluids can be drawn through each zone (e.g., using a vacuum or positive displacement pump, or the like), to capture the desired entities in the zones. The microenvironment of the capillary minimizes diffusion limitations thereby enhancing acceleration of the rate of binding of the ligand to the capturing agent.

Accordingly, CPG (Sigma Corporation, St. Louis, Mo.) was reacted with 3-aminopropyl trimethoxysilane (Sigma Corporation, St. Louis, Mo.) using standard published procedures. Subsequently, the amino modified glass was reacted with iminothiolane (Traut's reagent, Pierce Chemical Co., Rockford, Ill.). The latter procedure provides a sulphydryl group (thiol) for further reaction with maleimido modified proteins, drugs, nucleotides and other entities so modified.

Maleimido horseradish peroxidase was reacted with 20 mg of iminothiolane CPG. After washing, small portions (2 mg×3) of the beads were loaded into a micro-capillary tube. Each zone was separated by an inert glass or plug. A chemiluminescent substrate (Duolux, Lumigen, Southfield, Mich.) was pulled rapidly into the capillary using vacuum. The tube was transferred to a light measuring device (NightOwl CCD light scanner) and the light output read for 1 sec. The results are shown in FIG. 13A. In either case, three illumination zones are indicated, thereby demonstrating the feasibility of the system. In a further iteration, an epitope of cardiac troponin I (P14 cTNI epitope, Research Genetics, Huntsville, Ala.), conjugated to thyroglobulin (porcine thyroglobulin, Sigma Corporation, St. Louis, Mo.) was reacted with CPG. An antibody (P3 cTNI antibody, Fortron Bioscience Inc., Morrisville, N.C.), conjugated to peroxidase or alkaline phosphatase (AP), was introduced into the requisite capillary, excess conjugate was removed through rapid washing and the bound antibody enzyme visualized with an appropriate chemiluminescent substrate. The results are recorded in FIGS. 13B and 13C.

A single peroxidase bead, 100-200 microns in diameter, was exposed to Duolux and the light output recorded, compared with substrate background. The calculated signal to noise ratio was 3.5, indicating that the system has the potential of being reasonably sensitive. The results are shown in FIG. 14A.

In order to provide a generic CPG system, maleimido-neutravidin (neutravidin and maleimido peroxidase were purchased from Pierce Chemical Co., Rockford, Ill.) was reacted with iminothiolane glass. Neutravidin binds biotinylated species aggressively. Such biotinylated species include peptides, proteins, drugs, nucleotides and other entities so modified. In this example, biotin containing Stat 1 and phosphorylated Stat 1 antibodies (Stat1{pY$^{701}$} peptide, BioSource International, Camarillo, Calif.) were attached to CPG. Bovine serum albumin (Sigma Corporation, St. Louis, Mo.) containing phosphorylated Stat 1 peptide was drawn into a capillary, in which a zone of each was antibody was deposited. After washing, the zones were probed with RC20-AP (RC20-AP antibody conjugate purchased from Transduction Laboratories, Lexington, Ky.). Following a further wash, substrate was introduced and the light output recorded. In this experiment it was anticipated that the luminescence from the p-Stat 1 zone would be greater than that from the Stat 1 zone. This turned out to be the case. The light output from the Stat1 zone is related to the poor quality of the RC-20 AP conjugate and probably represents non-specific binding to the bound matrix antibody. To demonstrate that binding to a zone is reversible in the presence of a appropriate ligand, p-Stat 1 antibody beads were exposed to p-Stat 1 peptide peroxidase, both in the absence and presence of p-Stat1 peptide albumin (blocking agent). As anticipated, the presence of the peptide reduced the binding of the conjugate, resulting in less light output. The results are shown in FIG. 14B.

Figure 15:
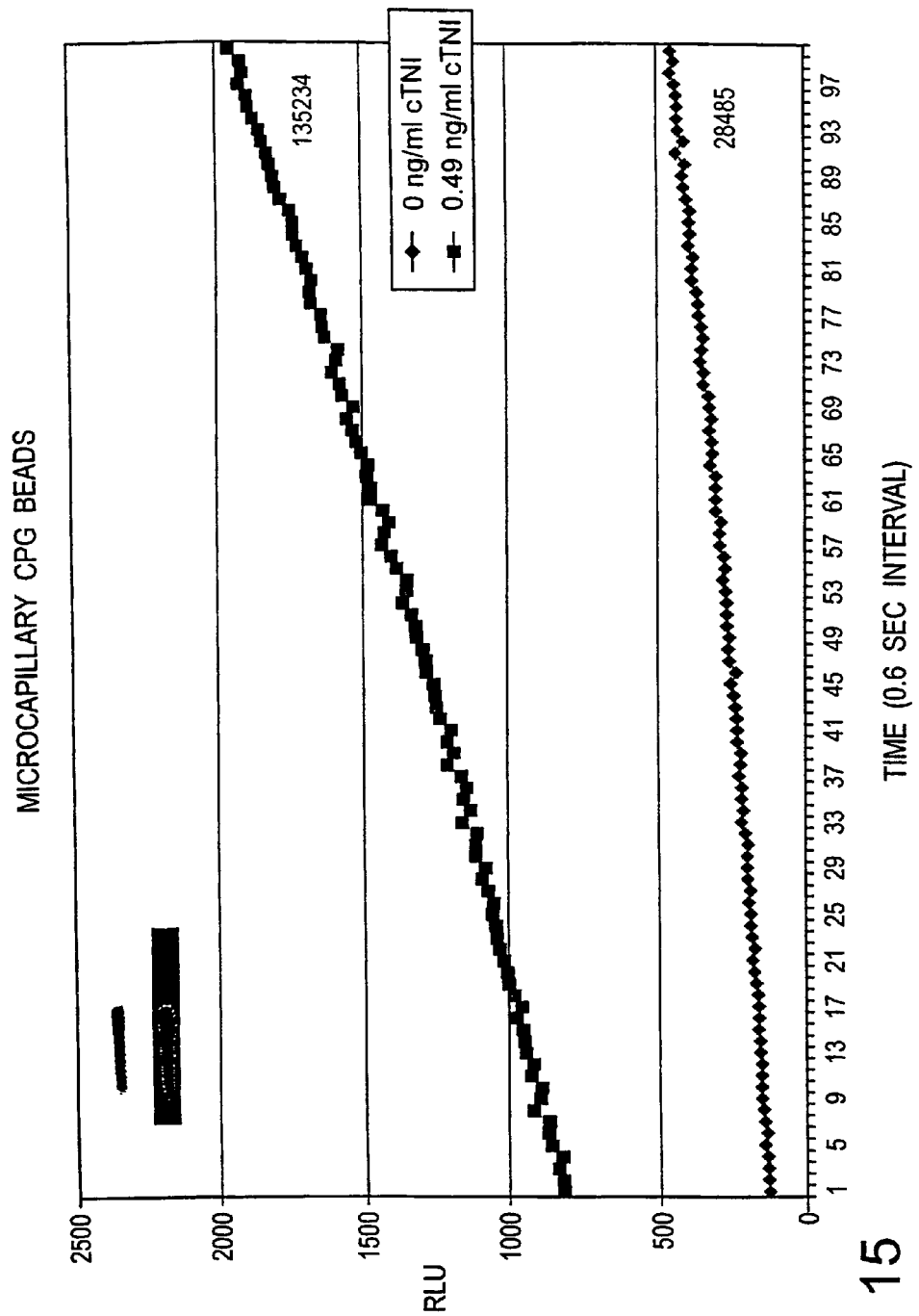

To further demonstrate the utility of our CPG capillary approach, neutravidin beads were reacted with a biotinylated antibody which recognizes a specific epitope on cardiac troponin I (cTNI). A negative serum sample was drawn through the capillary (vacuum). After washing, a secondary AP labeled antibody, with a different specificity for cTNI was introduced and excess conjugate removed immediately by washing. Exposure of the beads to substrate produced the light output shown in FIG. 15 (-◊-). Using the same capillary and procedure, a positive sample of cTNI (490 pg/ml) was examined for light yield (-□-). The calculated signal to noise ratio of 5 to 1 indicates that the system is capable of extreme sensitivity. An overlay of the light output from the capillary is included in FIG. 15.

Peripheral blood lymphocytes (PBLs) were exposed to alpha-interferon. The cells were lysed and cellular debris removed by centrifugation. In a similar fashion, non-treated cells were and lysed and the cell contents collected. Fifty microliters of each lysate were drawn through separate capillaries, each containing Stat 1 antibody CPG beads. The capillaries were probed with RC20-AP. After washing, substrate (CDP*) was drawn into the tubes and the light emission recorded in a tube luminometer (Junior Luminometer, Berthold Technologies) or the Nightowl CCD scanner. The data indicates that stimulation of PBLs with interferon, induces an increase of phosphorylated tyrosine species, which bind to Stat 1 protein. This is indicative of binding of tyrosine phosphorylated Stat 2 to Stat 1, thus forming the recognized heterodimer, known to be part of the alpha-interferon/lymphocyte signaling cascade. The results are illustrated in FIG. 16

An additional approach to confirm the observations from FIG. 16 is described here and shown in FIG. 17. Instead of probing with RC20-AP, a non-labeled mouse antibody specific for phosphorylated tyrosine in conjunction with a goat anti-mouse AP conjugate were employed sequentially. Negatively and positively, alpha-interferon stimulated PBL lysates were drawn through individually packed capillaries containing Stat 1 antibody CPG. After washing, etc., and exposure to the primary and secondary antibodies, the beads were exposed to CDP* substrate. The increase in positive light emission supports our contention that stimulation of PBLs with alpha-interferon leads to an increase in phosphorylated Stat2, which in turn binds to Stat 1 protein.

The phosphatase activity of PBLs is significantly reduced in the presence of pervanadate. Inhibition of phosphatase activity enhances the overall level of phosphorylated proteins within the lymphocyte. The experiment shown and described with reference FIG. 18 illustrates this phenomenon quite nicely. Briefly, CPG Stat 1 antibody beads (10 mg), were placed in a Z-spin well (Z-spin columns were obtained from Fisher Scientific, Pittsburgh, Pa.). As a control, plain neutravidin CPG was used. To each well, 50 µl of pervanadate treated PBL lysate was added. The wells were centrifuged, washed and then exposed sequentially to mouse anti-phosphorylated tyrosine antibody and goat anti-mouse AP conjugate. Each addition was followed by a wash/centrifuge cycle. The addition of CDP* substrate induced light emission which was recorded in the NightOwl. The data indicates that inhibition of phosphatase activity enables measurement of the basal level of phosphotyrosine proteins in non stimulated PBLs. In this instance, the data suggest that this type of methodology is capable of discriminating phosphorylated Stat2 from a whole range of known and as yet unknown phosphorylated signaling intermediates.

The following are experimental examples of more than 20 specific different trapping ligands that were successfully used in the subject invention for protein network profiling. The invention methods led to identification of phosphorylated proteins and assignment of their functional participation in signal pathways. The information derived is relevant to the following: a) identifying specific protein-protein interactions; b) assignment of the specific interactions into larger functional circuits and networks; c) downstream ordering of protein components in a given pathway; d) specific disruptions caused by drug treatments, disease, or toxicity; and e) identifying patterns of protein interactions or phosphorylations that are unique to disease state, drug treatment or toxicity.

1. 100,000 primary human lymphocytes and 100,000 primary human monocytes obtained by tangential centrifugal elutriation and differential ficoll-percoll gradient selection were resuspended in 5 ml (each cell type) RPMI-1640 media.

2. 1 ml aliquots were placed in eppendorf tubes

3. A 100× cocktail (herein referred to as PI or phosphatase inhibitor cocktail) consisting of the following: 2500 nM Okadaic acid (cell-permeable inhibitor of protein phosphatase); 500 micromolar sodium pervandate (membrane soluble form of sodium orthovanadate and an inhibitor of tyrosine phosphatases), 500 nM Calyculin A (cell-permeable inhibitor of protein phosphatase 2A and protein phosphatase); and 2500 micromolar phenylarsine oxide (cell-permeable phosphotyrosine phosphatase inhibitor).

4. The following experimental treatment protocol was then set up and performed with each 1 ml cell suspension (20,000 cells/ml):

i. primary human lymphocytes/monocytes+vehicle alone (10 microliters DMSO) 1 hour;

ii. primary human lymphocytes/monocytes+1×PI ½ hour; and iii. primary human lymphocytes/monocytes+1×PI ½ hour+10 micromolar SB 203589 (p38 kinase inhibitor) ½ hour.

5. Cells were pulse centrifuged at 5000×g for 2 minutes, washed twice in ice cold PBS and the resultant cell pellet lysed in 100 microliters lysing solution (TPER (Pierce Chemical)+2 mM sodium orthovanadate (tyrosine phosphatase inhibitor), 10 mM B-glycerol phosphate (serine phosphatase inhibitor), 300 mM NaCl, 4 NM AEBSF (protease inhibitor)), vortexed rapidly for 1 minute and clarified by centrifugation for 5 minutes.

At this point the lysates are analyzed by 4 main methods.
   i. Open faced array of antibodies immobilized on nitrocellulose (see No. 6 list below).
   ii. Flow-through devices striped with trapping zones containing protein binding ligands.

The analysis was complemented by the following additional standard methods:
   iii. Two-dimensional or one-dimensional gel-based separation technologies.
   iv. Mass-spectrophotometric-based baiting technologies.

6. The resultant whole cell lysate was then incubated overnight at 4 degrees C. on an Oncyte multiwell (Grace Biolabs, Inc) nitrocellulose slide that was spotted with rabbit polyclonal phospho-specific antibodies recognizing the following 20 proteins: EGFR (Tyr1173); Tyk2 (Tyr1054/1055); ATF-2 (Thr71); eIF2a (Ser51); eIF4E (Ser209); Cdc2 (Tyr15); p38 (Thr180/Tyr182); Cdk1 (Thr14/Tyr15); CREB (Ser133); Akt (Ser473); eNOS (Ser1177); CREB (Ser133); c-Jun (Ser63); Elk-1 (Ser383); ErbB2 (Tyr1248); Bad (Ser112); Jak1 (Tyr1022/1023); p70 S6 (Thr421/Ser424); ERK1/2 (Thr202/Tyr204); and Cdc25 (Ser216).

7. The slide was washed 3× with TBC-tween for 5 minutes, then incubated with a horseradish peroxidase-conjugated goat anti-rabbit antibody for 1 hour at 4 degrees C.

8. Chemiluminescent detection was performed using the ECL-plus kit from Amersham following recommended manufacturer procedures.

9. Proteins whose phosphorylation is dependent upon p38 kinase activity and lie downstream of the p38 kinase are subsequently identified by their inhibition of phosphorylation due to the pre-incubation of the specific p38 kinase inhibitor.

10. For 2D-PAGE applications, the lysates are enriched for phosphorylated proteins via:
   i. Affinity chromatography-based or immuno-precipitation-based methods (i.e., using a anti-phosphotyrosine antibody, anti-phosphoserine antibody, etc.); and
   ii. Eluted by a competitive mimetic such as phenylphosphate or sodium pyrophosphate or a specific peptide used as the antigen for the development of the antibody.
   iii. The resultant eluate is then run on the gels directly, and phosphorylated proteins detected by traditional staining procedures compatible with mass spectroscopy-based protein identification (e.g., colloidal coomassie, ponceau S, SYPRO Ruby-red (Molecular Probes, Eugene, Oreg.), and so forth).
   iv. The visualized proteins are identified by mass spectroscopy and proteins whose activity lie downstream and are substrates for the p38 kinase are identified by the absence of the signal on the gel which separated lysates that were pretreated with the specific kinase inhibitor.

11. For flow-through applications see the previous example for IFNA and ERB2.

12. For mass-spectrophotometric applications a Ciphergen Inc. mass spec. instrument was employed.

The resultant phosphoprotein-enriched eluates or whole cell extracts are incubated on bait traps that specifically bind phosphorylated proteins. Such baits may be protein-based (e.g., anti-phosphotyrosine antibody) or chemical (e.g., iron, gallium ion, etc.). The surfaces are then washed and phosphorylated proteins detected and identified by time-of-flight or collision-induced daughter ion spectral analysis.

Novel circuit profiles and maps were successfully obtained using ligands that recognized the phosphorylated versions of the 20 proteins listed in above.

1. The following proteins were identified to lie downstream of p38 kinase: CREB, CD25, cJUN, Cdk1, and e1f2A.

2. The following proteins can be activated in primary human monocytes: EGFR, Tyk2, E1F2a, E1F4E, p38, CDK1, CREB, c-Jun, Elk-1, BAD, Jak1, Erk 1/2, CD25. The following were specific to monocytes and not found in lymphocytes from the same patient: EGFR, Tyk2, E1F2a.

3. The following proteins are specifically activated in primary human lymphocytes but not monocytes from the same patient: ERB2.

4. The following new unknown proteins changed their phosphorylation state in response to treatment with SB203589: mw. 100 kDa; mw. 85 kDa; mw. 35 kDa; mw. 30 kDa; mw. 25 kDa; mw. 20 kDa.

5. ERB2 positive primary human breast cancer cells show that ERK is interacting and binding with the following proteins to a greater level than ERB2 negative human breast cancer cells: pERB2, pERB1, pELK, p70S6K.

6. Fresh human brain and prostate tissue cells can be treated ex vivo with phosphatase inhibitors under the subject invention resulting in the identification of proteins that are phosphorylated in a tissue and disease specific manner.

Figure 19:
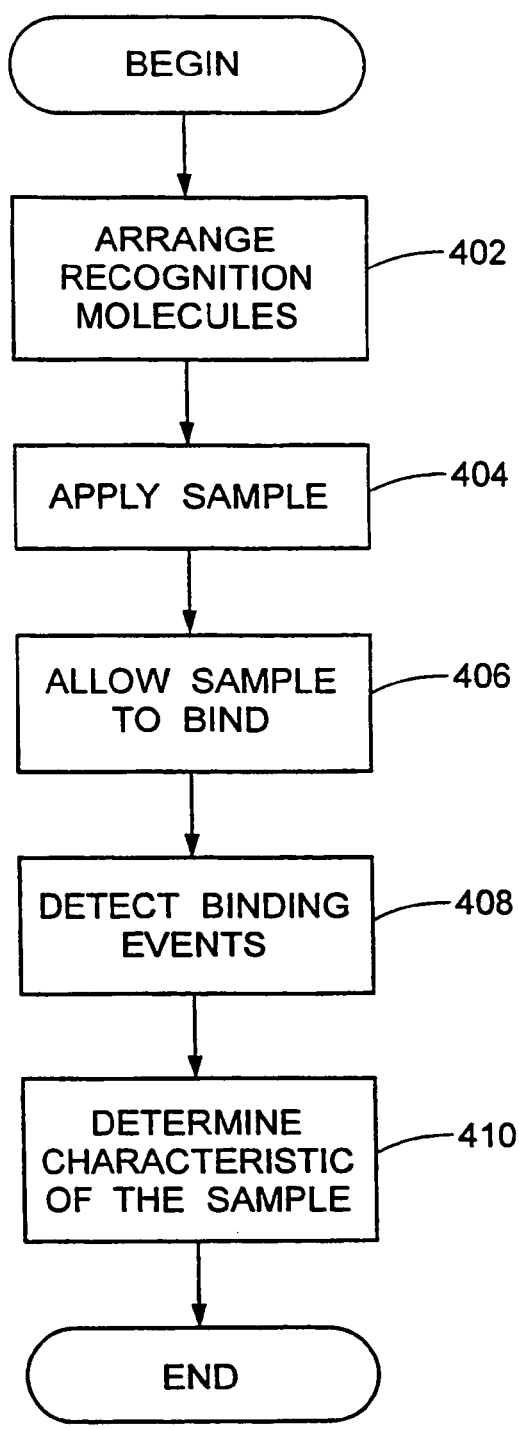
FIG. 19 is a flow chart of a signal transduction pathway profiling method in accordance with the present invention.

FIG. 19 is a flow chart of a molecular detection method in accordance with the present invention. As indicated in step 402, the method includes arranging a series of recognition molecules or binding reagents which selectively bind to the various proteins, their phosphorylated or activated state, and their binding partners, of a signal transduction pathway to form a signal transduction pathway profiling chip 100 as described above by way of reference to FIG. 1. The method further includes applying (step 404) a cell lysate from a tissue of interest to the profiling chip. Thereafter, the sample is allowed to bind or hybridize with the recognition molecules at the binding sites 116 (FIG. 1) as indicated by step 406.

At step 408, binding events at the plurality of binding sites 116 are detected. The detection can be performed by a number of labeling or other techniques to produce a detectable signal, such as spectrophotometric, fluorometric, colorimetric, chemiluminescent, radiometric, electrochemical, photochemical, enzymatic, or optical readout techniques, and the like. In one embodiment, the step of detecting the binding events provides a qualitative indication of binding at each binding site. More preferably, however, a quantitative determination of binding at each binding site is made at step 408, for example, by determining an intensity or magnitude of the detectable signal at each binding site.

Figure 20:
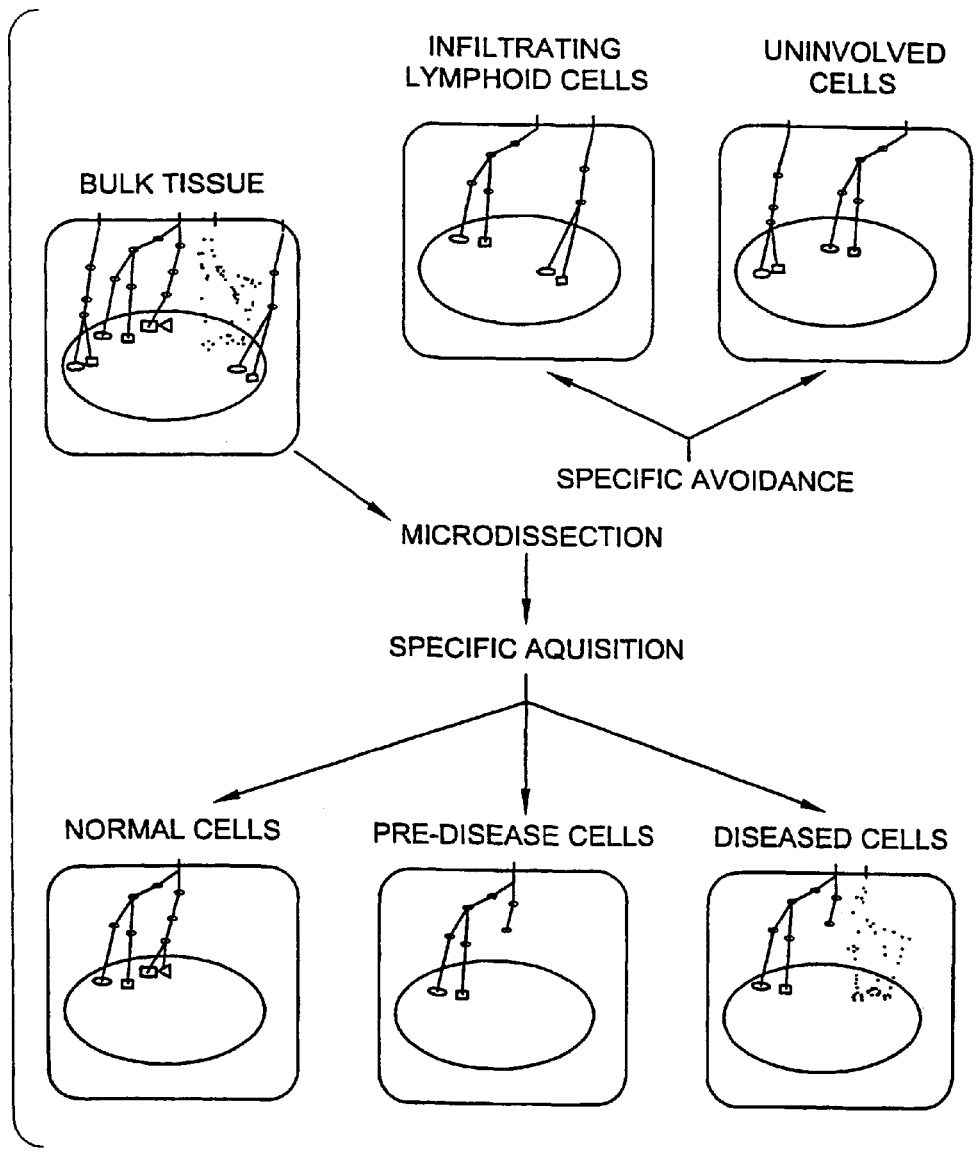
FIGS. 20 and 21 illustrate the use of patterns for the identification of a pathway and/or disease state of a cell sample.
Figure 21:
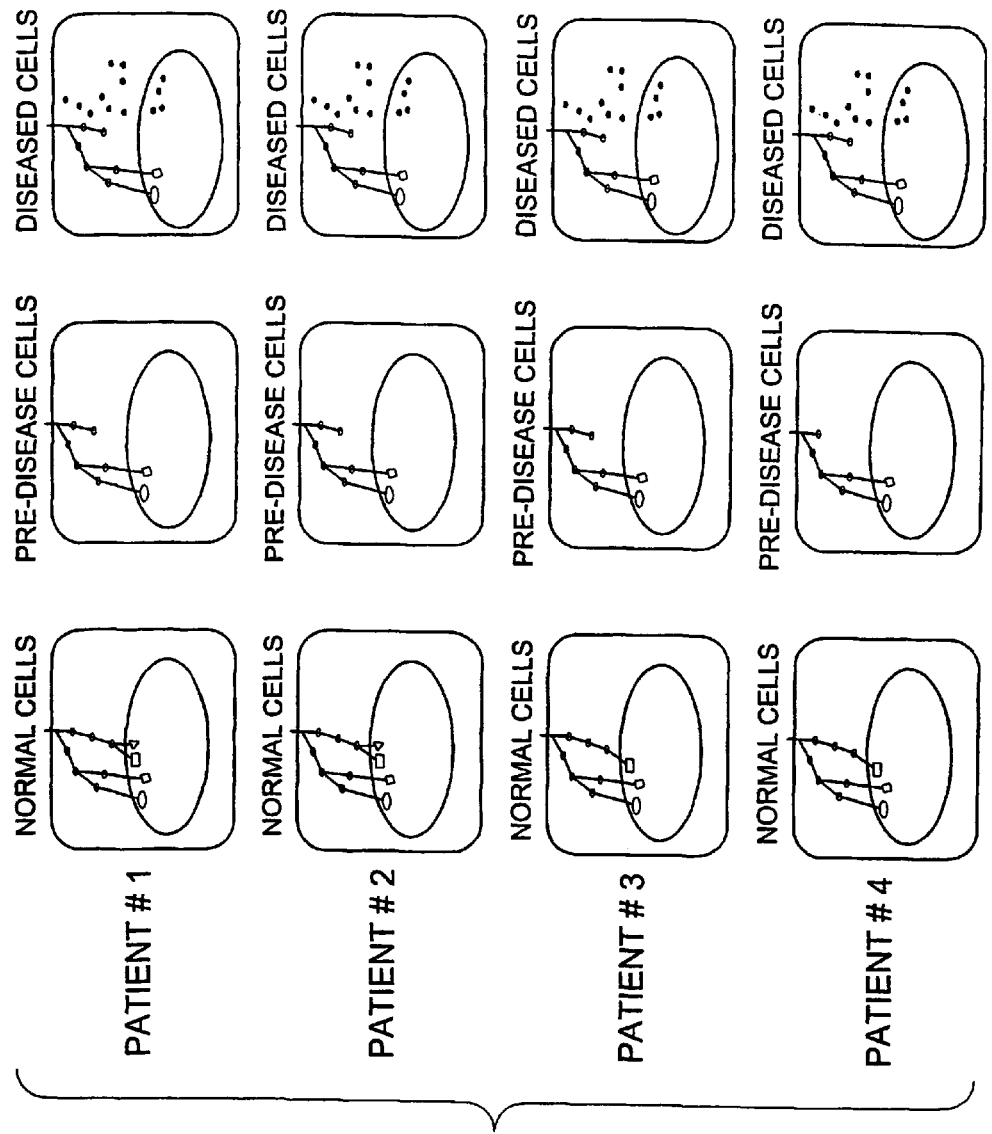

At step 410, the detected binding events are used to determine a characteristic of the analyzed sample. By identifying at which sites binding events occurred, the status of the selected pathway can be determined. The determination can be made by visual detection of the binding sites. Alternately, the characteristics can be determined automatically, for example, using a binding event sensor and pattern recognition software so that the pathway status can be determined under preprogrammed control. Furthermore, heuristic algorithms are used to correlate binding patterns and/or pathway status with cellular conditions, such as normal, pre-disease, or disease states. The use of patterns for the identification of a pathway and/or disease state of a cell sample is illustrated in FIGS. 20 and 21.

Appendix A of 17 pages is incorporated herein by reference. Appendix A presents further exemplary embodiments related to the protein interaction profiling system and method of the present invention.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

What is claimed is:

1. A method for assessing a status of a selected signal transduction pathway in cells, comprising:
   a) generating a lysate of cells containing one or more phosphorylated molecules that reflect signal transduction events taking place in the cells;
   b) applying the lysate to a molecular detection device, the device including
      i) a common chase application zone;
      ii) a common waste outlet region; and
      iii) a plurality of support members, each support member having a lysate application zone and an immobilized series of different antibodies which are selected and arranged in zones to discriminate between one or more phosphorylated pathway molecules for the selected signal transduction pathway, wherein the immobilized antibodies are specific for a plurality of the following proteins:
      EGFR, Tyk2, ATF-2, eIF2a, eIF4E, Cdc2, p38, Cdk1, CREB, Akt, eNOS, c-Jun, Elk-1, ErB2, Bad, Jak1, p70 S6, ERK1/2, and Cdc25,
   and the selected signal transduction pathway is the epidermal growth factor (EGF) receptor pathway;
   c) identifying binding events between the phosphorylated pathway molecules and the immobilized antibodies; and
   d) determining the status of the selected signal transduction pathway;
   wherein the common chase application zone is situated above the plurality of support members; and
   wherein the common waste outlet region is situated below the plurality of support members.

2. The method of claim 1, wherein the determining step further comprises comparing the identified patterns of binding events with one or more previously identified patterns for cells of a known condition.

3. The method of claim 2, wherein the molecular detection device is a flow-through matrix to which the antibodies are immobilized, the matrix enabling different protein complexes containing the same phosphorylated pathway molecule to be identified.

4. The method of claim 3, wherein the antibodies are arranged in reverse temporal order of the selected signal transduction pathway.

5. The method of claim 3, wherein the antibodies are arranged in forward temporal order of the selected signal transduction pathway.

6. The method of claim 1, further comprising:
   e) capturing the lysate after the lysate has been applied to the molecular detection device; and
   f) determining the identity of remaining unknown phosphorylated proteins left undetected by the molecular detection device in the captured lysate.

7. The method of claim 1, wherein the identifying binding events includes querying the zones with a tagged or detectably labeled antibody to generate a signal.

8. A method for assessing a status of a epidermal growth factor (EGF) receptor signal transduction pathway in cells, comprising:
   a) generating a lysate of cells containing a plurality of different phosphorylated molecules that reflect signal transduction events taking place in the cells;
   b) applying the lysate to a molecular detection device, the device including:
      i) a common chase application zone;
      ii) a common waste outlet region; and
      iii) a plurality of support members, each support member having a lysate application zone and an immobilized series of different binding reagents which are selected and arranged in zones to determine the status of the EGF receptor signal transduction pathway, wherein the binding reagents are antibodies specific for the following proteins: c-myc, c-jun, p70RSK, erk, AKT, c-RAF, erb2, and erb1;
   c) identifying binding events between phosphorylated pathway molecules and the binding reagents; and
   d) determining the status of the EGF receptor signal transduction pathway;
   wherein the common chase application zone is situated above the plurality of support members; and
   wherein the common waste outlet region is situated below the plurality of support members.

\* \* \* \* \*